United States Patent [19]

Kieffer

[11] Patent Number: 4,579,988

[45] Date of Patent: Apr. 1, 1986

[54] PROCESS FOR THE PREPARATION OF AN AROMATIC HYDROCARBON MIXTURE

[75] Inventor: Eduard P. Kieffer, Amsterdam, Netherlands

[73] Assignee: Shell Oil Company, Houston, Tex.

[21] Appl. No.: 638,815

[22] Filed: Aug. 8, 1984

[30] Foreign Application Priority Data

Aug. 8, 1983 [NL] Netherlands .................... 8302789

[51] Int. Cl.$^4$ ............................................. C07C 2/00
[52] U.S. Cl. .................... 585/415; 585/407; 502/61; 502/71
[58] Field of Search .............. 585/407, 415, 417; 502/61, 71

[56] References Cited

U.S. PATENT DOCUMENTS

| | | | |
|---|---|---|---|
| 3,760,024 | 9/1973 | Cattanach | 585/415 |
| 3,843,741 | 10/1974 | Yan | 585/415 |
| 3,845,150 | 10/1974 | Yan et al. | 585/415 |
| 4,180,689 | 12/1979 | Davies et al. | 585/415 |

Primary Examiner—John Doll
Assistant Examiner—A. Pal
Attorney, Agent, or Firm—Kimbley L. Muller

[57] ABSTRACT

A process is disclosed for converting $C_2$-$C_4$ paraffins into aromatic gasoline over a crystalline gallium silicate having a $SiO_2/Ga_2O_3$ molar ratio between 25 and 250, which silicate has been subjected once or several times to a two-stage treatment comprising reduction at a temperature of 400°–650° C. and oxidation at a temperature of 350°–700° C. Optionally the gallium silicate is subjected to precalcining at a temperature of 600°–1000° C., the number of times of the two-stage treatment being determined by the fact whether or not said gallium silicates have been subjected to such precalcination.

20 Claims, No Drawings

PROCESS FOR THE PREPARATION OF AN AROMATIC HYDROCARBON MIXTURE

BACKGROUND OF THE INVENTION

The invention relates to a process for the preparation of an aromatic hydrocarbon mixture from paraffins having two, three or four carbon atoms per molecule, or from aliphatic hydrocarbon mixtures consisting more than 50%w of said paraffins, by using a catalyst containing a crystalline metal silicate of a special structure.

Olefins having two, three or four carbon atoms per molecule can be converted at a relatively low temperature and in high yields into aromatic hydrocarbon mixtures by contacting the olefins with a crystalline metal silicate of a special structure. The crystalline metal silicates concerned are characterized in that (a) they have been prepared by crystallization from an aqueous mixture which, in addition to the components needed for synthesizing the silicate, comprises one or more compounds of a trivalent metal X chosen from the group formed by aluminum and iron, in such quantities that in the formula which represents the composition of the silicate expressed in moles of the oxides, the $SiO_2/X_2O_3$ molar ratio of 10–500, and (b) after one hour's calcination in air at 500° C. they have an X-ray powder diffraction pattern in which the strongest lines are in four lines mentioned in Table A,

TABLE A

| d(Å) |
| --- |
| 11.1±0.2 |
| 10.0±0.2 |
| 3.84±0.07 |
| 3.72±0.06 |

A similar conversion into aromatic hydrocarbon mixtures of paraffins having two, three of four carbon atoms per molecule and of aliphatic hydrocarbon mixtures consisting more than 50%w of said paraffins (for the sake of brevity hereinafter referred to as "the present conversion") is much more difficult to achieve and requires considerably higher temperatures, which accounts for the important role played by cracking reactions and for the yields of $C_5+$ hydrocarbons remaining low. During the present conversion hydrogen is released. In view of the growing demand for hydrogen for a variety of purposes, it is important that in the present conversion as much of the hydrogen as possible becomes available as molecular hydrogen instead of hydrogen-rich byproducts, such as methane. It has been found that the above-mentioned crystalline aluminum silicates show very low $C_5+$ and $H_2$ selectivities. The crystalline iron silicates have very low activity and, in addition, a low to very low $C_5+$ selectivity. This is true both of the crystalline metal silicates with a high metal content ($SiO_2/X_2O_3$ molar ratio <100) and of the crystalline metal silicates with a low metal content ($SiO_2/X_2O_3$ molar ratio >100). A solution to the low activity and low selectivity problem of the present conversion may be found in a two-step process in which in the first step the paraffins are converted into olefins by dehydrogenation, followed in the second step by conversion of these olefins over the above-mentioned crystalline aluminum and iron silicate catalysts. Naturally, for carrying out the present conversion on a technical scale a one-step process is much to be preferred to a two-step process; therefore, in spite of the above-described disappointing results with the crystalline aluminum and iron silicates of a special structure (as characterized in Table A), an extensive investigation was carried out to determine whether by introducing certain changes in the composition of the metal silicates without affecting their special structure products can be prepared which are suitable for use as catalysts for carrying out the present process in a single step. The investigation has surprisingly shown that compositions containing both gallium and a crystalline metal silicate of the afore-mentioned special structure—provided that they meet certain conditions with regard to the gallium content and the way in which the gallium has been incorporated into the composition, as well as to possible subjection of the gallium-containing composition to one or more two-step treatments—are excellently suitable for use as catalysts for carrying out the present conversion in a single step. Either per se or after having been subjected to one or more two-step treatments said gallium-containing catalysts have both high activity and high $C_5+$ and $H_2$ selectivities.

The gallium-containing catalysts which,—whether after one or more two-step treatments or not—are eligible for use in the present conversion can be arranged in the following two classes based on the manner in which the gallium is present in the catalysts:

I. Catalysts containing a crystalline gallium silicate which is characterized in that (a) it has been prepared by crystallization from an aqueous mixtures which, in addition to the components needed for synthesizing the silicate, comprises one or more gallium compounds and, if desired, one or more compounds of a trivalent metal Y chosen from the group formed by aluminum, iron, cobalt and chromium, in such quantities that in the formula which represents the composition of the silicate expressed in moles of the oxides, the $SiO_2/Ga_2O_3$ molar ratio is 25–250 and the $Y_2O_3/Ga_2O_3$ molar ratio is lower than 1, and (b) after one hour's calcination in air at 500° C. it has an X-ray powder diffraction pattern in which the strongest lines are the four lines mentioned in Table A.

II. Catalysts containing gallium supported on a carrier and a crystalline metal silicate which is characterized in that (a) it has been prepared by crystallization from an aqueous mixture which, in addition to the components needed for synthesizing the silicate, comprises one or more compounds of a trivalent metal Y chosen from the group formed by aluminum, iron, cobalt and chromium and, if desired, one or more gallium compounds, in such quantities that in the formula which represents the composition of the silicate expressed in moles of the oxides, the $SiO_2/(Y_2O_3+Ga_2O_3)$ molar ratio is 10–500 and the $Ga_2O_3/Y_2O_3$ molar ratio is lower than 1, and (b) after one hour's calcination in air at 500° C. it has an X-ray powder diffraction pattern in which the strongest lines are the four lines mentioned in Table A, in which catalysts the quantity of gallium which occurs supported on a carrier firstly amounts to 0.3–10%w, calculated on the sum of the quantity of crystalline metal silicate present in the catalyst and the quantity of other material used as carrier for the gallium which may be present in the catalyst, and secondly amounts to 1–10%w, calculated on the amount of crystalline metal silicate present in the catalyst.

As regards the composition, the main difference between the catalysts belonging to Classes I and II is the fact that the gallium present in the catalysts belonging to Class I occurs in the crystalline silicate of a special structure alone and has been incorporated therein during the preparation of the silicate by crystallization from an aqueous mixture containing one or more gallium compounds, whereas in the case of the catalysts belonging to Class II at least part of the gallium present therein occurs as a deposit on a carrier. A carrier for the gallium that may suitably be used is the crystalline silicate of a special structure present in the catalysts belonging to Class II, onto which the gallium has been deposited for instance by impregnation or ion exchange. In the catalysts belonging to Class II the gallium occurring may be partly or wholly deposited on a conventional carrier, such as silica, the gallium-loaded carrier being present in the catalyst in admixture with a crystalline silicate of a special structure. Just as in the case of the crystalline silicates present in the catalysts belonging to Class I it holds that the aqueous mixture from which they are prepared by crystallization may contain, in addition to one or more gallium compounds, a minor quantity of one or more compounds of trivalent metals Y, so in the case of the crystalline silicates present in the catalysts belonging to Class II it holds that the aqueous mixture from which they are prepared by crystallization may contain, in addition to one or more compounds of a trivalent metal Y, a minor quantity of one or more gallium compounds.

With regard to the differences in performance existing between the catalysts belonging to class I when used in the present conversion, these catalysts may be further divided into a class IA and a class IB, depending on the $SiO_2/Ga_2O_3$ molar ratio of the crystalline gallium silicate present therein. The catalysts belonging to class IA are characterized in that the crystalline gallium silicate that they contain has a $SiO_2/Ga_2O_3$ molar ratio lower than 100. In the catalysts belonging to class IB the $SiO_2/Ga_2O_3$ molar ratio of the crystalline gallium silicate present therein is at least 100.

It has been found that the catalysts belonging to class IA have a very high activity as well as very high $H_2$ and $C_5^+$ selectivities. Consequently, they are excellently suitable to be used per se as catalysts for carrying out the present conversion.

It has been found that the catalysts belonging to class IB have a relatively low activity and a low to very low $C_5^+$ selectivity. This makes them less suitable for use in carrying out the present conversion such as they are. However, further investigation into this subject has revealed that the performance of these catalysts in carrying out the present conversion can be greatly enhanced by subjecting them once or several times to a two-step treatment. This treatment leads to a substantial increase in activity and $H_2$ and $C_5^+$ selectivities and renders it possible, starting from the catalysts belonging to class IB which as such are not suitable for use in carrying out the present conversion, to produce catalysts whose activity and $H_2$ and $C_5^+$ selectivities lie at a level comparable to that of the catalysts belonging to class IA. The investigation has further shown that if the treatment found for the catalysts belonging to class IB is applied to the catalysts belonging to class IA (which in themselves have a very high activity and very high $H_2$ and $C_5^+$ selectivities), a considerable additional gain in activity and $C_5^+$ selectivity can be achieved for the latter catalysts as well. The invention therefore in the first place relates to carrying out the present conversion by using a catalyst belonging to class I (class IA as well as class IB) which has been subjected once or several times to a two-step treatment.

It has been found that the catalysts belonging to class II have a very low $C_5^+$ selectivity. This renders them rather unsuitable to be used per se in carrying out the present conversion. However, continued investigation into this subject has shown that the performance of these catalysts when carrying out the present conversion can be much improved by subjecting them once or several times to a two-step treatment. This treatment results in a substantial increase of the $C_5^+$ selectivity. In addition the treatment leads to enhancement of the activity and $H_2$ selectivity of the catalysts. Using a two-step treatment renders it possible, starting from catalysts belonging to class II, which on account of their low $C_5^+$ selectivity are unsuitable to be used per se in carrying out the present conversion, to obtain catalysts which are very suitable for the purpose. The invention therefore further relates to carrying out the present conversion by using a catalyst belonging to class II which has been subjected once or several times to a two-step treatment.

The liquid hydrocarbon mixtures obtained in the present conversion boil substantially in the gasoline range and have a very high octane number. They are therefore excellently suitable for use as motor gasoline or as mixing components for motor gasolines.

The treatment of a catalyst belonging to class I involves subjecting the catalyst once or several times to a two-step treatment comprising a step in which the catalyst is contacted for at least 15 minutes and at a temperature of 400°–650° C. with a reducing gas which contains at least 20%v hydrogen, followed by a second step in which the catalyst is contacted for at least 15 minutes and at a temperature of 350°–700° C. with an oxidizing gas containing at least 5%v oxygen. According as the catalysts belonging to class I are subjected to the two-step treatment more often, their performance in the present conversion will improve. This improvement progresses until a certain maximum level has been reached, where further repetition of the two-step treatment ceases to produce any effect. The minimum number of times that catalysts belonging to class I should be subjected to the two-step treatment in order to raise their performance in the present conversion to an acceptable level is dependent on the $SiO_2/Ga_2O_3$ molar ratio of the silicate present therein, and for catalysts in which the silicate has a $SiO_2/Ga_2O_3$ molar ratio higher than 110 it is given by the formula $$n = \frac{m - 100}{10},$$

wherein n represents the minimum number of two-step treatments and m the $SiO_2/Ga_2O_3$ molar ratio of the silicate. As regards the catalysts belonging to class I, it has surprisingly been found that the number of times that the two-step treatment has to be carried out in order to carry their performance to a certain desired high level can be considerably decreased if, before being subjected to a succession of two-step treatments, the catalysts are exposed to calcination at a temperature of 600°–1000° C. have to be subjected to the two-step treatment in order to carry their performance in the present conversion to an acceptable level again depends on the $SiO_2/Ga_2O_3$ molar ratio of the silicate present therein, and for catalysts in which the silicate has a $SiO_2/Ga_2O_3$ molar ratio higher than 130 it is given by the formula $$n = \frac{m - 100}{10},$$

wherein n and m have the meanings mentioned hereinbefore. In this connection it should be noted that when the above formulae produce a value for n which can be expressed as the sum of a natural number N and a fractional number smaller than 1, the minimum number of times that the catalyst should be subjected to the two-step treatment is N+1.

Carrying out the present conversion by using a catalyst belonging to class I which has been subjected once or several times to the two-step treatment described hereinbefore forms the subject matter of the present patent application.

Carrying out the present conversion by using a catalyst belonging to class II which has been subjected once or several times to a two-step treatment forms the subject matter of Netherlands patent application No. 8302788.

SUMMARY OF THE INVENTION

The present patent application therefore relates to a process for the preparation of an aromatic hydrocarbon mixture, in which one or more paraffins with two, three or four carbon atoms per molecule or aliphatic hydrocarbon mixtures consisting more than 50%w of said paraffins are contacted with a catalyst containing a crystalline gallium silicate which (a) has been prepared by crystallization starting from an aqueous mixture which, in addition to the components needed for the synthesis of the silicate, comprises one or more gallium compounds and, if desired, one or more compounds of a trivalent metal Y chosen from the group formed by aluminum, iron, cobalt and chromium, in such quantities that in the formula which represents the composition of the silicate expressed in moles of oxides, the $SiO_2/Ga_2O_3$ molar ratio is 25–250 and the $Y_2O_3/Ga_2O_3$ molar ratio is lower than 1, and (b) after one hour's calcination in air at 500° C. has an X-ray powder diffraction pattern in which the strongest lines are the four lines mentioned in Table A,

TABLE A

| d(Å) |
| --- |
| 11.1±0.2 |
| 10.0±0.2 |
| 3.84±0.07 |
| 3.72±0.06, | in which the catalyst has been subjected once or several times to a two-step treatment involving a step in which the catalyst is contacted for at least 15 minutes and at a temperature of 400°–650° C. with a reducing gas containing at least 20%v hydrogen, followed by a second step in which the catalyst is contacted for at least 15 minutes and at a temperature of 350°–700° C. with an oxidizing gas containing at least 5%v oxygen, in which, before being subjected to the two-step treatment or a succession of two-step treatments, the catalyst is optionally calcined at a temperature of 600°–1000° C., in which for catalysts comprising a silicate with the $SiO_2/Ga_2O_3$ molar ratio higher than 110 which have not been subjected to previous calcination at 600°–1000° C. the minimum number of two-step treatments to be carried out is given by the formula $$n = \frac{m - 100}{10},$$

and in which for catalysts comprising a silicate with a $SiO_2/Ga_2O_3$ molar ratio higher than 130 which have been subjected to previous calcination at 600°–1000° C., the minimum number of two-step treatments to be carried out is given by the formula $$n = \frac{m - 100}{30},$$

on the understanding that if the afore-mentioned formula, in which n represents the minimum number of two-step treatments and m the $SiO_2/Ga_2O_3$ molar ratio of the silicate, produce a value for n which may be expressed as the sum of a natural number N and a fractional number smaller than 1, the minimum number of times that the catalyst should be subjected to the two-step treatment is N+1.

DETAILED DESCRIPTION OF THE INVENTION

Hereinafter, whenever mention is made of the term "the process according to the invention", it is used exclusively to designate the process in which the present conversion is carried out by using a catalyst belonging to class I which has been subjected once or several times to the two-step treatment described hereinbefore.

In the process according to the invention the starting material should be one or more paraffins having two, three or four carbon atoms per molecule or an aliphatic hydrocarbon mixture which consists more than 50%w of said paraffins. The paraffins with two, three or four carbon atoms per molecule which should constitute more than 50%w of the feed are ethane, propane, n-butane and isobutane. If the starting material is an aliphatic hydrocarbon mixture which, in addition to the paraffins mentioned, contains other aliphatic hydrocarbons as well, this mixture may contain, inter alia, methane, ethene, propene, butene, isobutene, butadiene and paraffins and olefins with five or more carbon atoms per molecule. In the process according to the invention the preferred starting material is a feed which consists more than 75%w, and in particular substantially completely, of one or more paraffins having three or four carbon atoms per molecule. A feedstock which is very suitable for use in the process is a mixture of paraffins with three and four carbon atoms per molecule obtained as a by-product in the production of mineral oil.

The process according to the invention is preferably carried out at temperature of 350°–700° C. and in particular of 450°–650° C., a pressure of 1–20 bar and in particular of 1–10 bar and a space velocity of 0.1–10 kg.kg$^{-1}$.hour$^{-1}$ and in particular of 0.5–5 kg.kg$^{-1}$.hour$^1$.

In the process according to the invention the feed is contacted with a catalyst containing a crystalline gallium silicate which is defined, among other things, by an X-ray powder diffraction pattern which the silicate shows after one hour's calcination in air at 500° C. In this pattern the strongest lines should be the four lines mentioned in Table A. The complete X-ray powder diffraction pattern of a typical example of the present crystalline gallium silicates after one hour's calcination in air at 500° C. is given in Table B.

TABLE B

| d(Å) | Rel. int. | d(Å) | Rel. int. |
|---|---|---|---|
| 11.1 | 100 | 3.84 (D) | 57 |
| 10.0 (D) | 70 | 3.72 (D) | 31 |
| 8.93 | 1 | 3.63 | 16 |
| 7.99 | 1 | 3.47 | <1 |
| 7.42 | 2 | 3.43 | 5 |
| 6.68 | 7 | 3.34 | 2 |
| 6.35 | 11 | 3.30 | 5 |
| 5.97 | 17 | 3.25 | 1 |
| 5.70 | 7 | 3.05 | 8 |
| 5.56 | 10 | 2.98 | 11 |
| 5.35 | 2 | 2.96 | 3 |
| 4.98 (D) | 6 | 2.86 | 2 |
| 4.60 | 4 | 2.73 | 2 |
| 4.35 | 5 | 2.60 | 2 |
| 4.25 | 7 | 2.48 | 3 |
| 4.07 | 2 | 2.40 | 2 |
| 4.00 | 4 | | |

(D) = doublet

Catalysts which are eligible for use in the process according to the invention are catalysts containing a crystalline gallium silicate having $SiO_2/Ga_2O_3$ molar ratio of 25-250.

Since investigation has shown that application of the two-step treatment according to the invention to catalysts containing a crystalline gallium silicate having a $SiO_2/Ga_2O_3$ molar ratio lower than 60 produces catalysts whose performance in the present conversion is not superior to that obtained when applying said treatment to catalysts containing a crystalline gallium silicate having a $SiO_2/Ga_2O_3$ molar ratio of 60-100, it is preferred, in view of the fairly high cost of gallium, in the process according to the invention, to use a catalyst containing a crystalline gallium silicate having a $SiO_2/Ga_2O_3$ molar ratio of at least 60.

As regards the number of times that the two-step treatment should be carried out in order to obtain a catalyst with acceptable or optimum performance in the present conversion, the following may be remarked.

In general the performance of catalysts containing a crystalline gallium silicate with a $SiO_2/Ga_2O_3$ molar ratio of at most 110 may be carried to an optimum level by subjecting the catalysts at most three times to the two-step treatment.

The minimum number of two-step treatments that have to be applied to catalysts containing a crystalline gallium silicate with a $SiO_2/Ga_2O_3$ molar ratio higher than 110 is given by the formula $$n = \frac{m - 100}{10}.$$

Subjecting the catalyst to a number of two-step treatments which corresponds to n in the formula (alternatively N+1) leads to the production of a catalyst with acceptable performance in the present conversion. As already remarked, the perfromance of a catalyst which, by the application of the number of two-step treatments given by the formula, has been raised to an acceptable level, can be enhanced still further to attain an optimum level by increasing the number of two-step treatments. The investigation has shown that the number of two-step treatments to which the catalyst should be subjected in order to attain optimum performance is about three times as much as the number of times (n, alternatively N+1) which, according to the formula, is the minimum required to achieve acceptable performance. For instance, in the case of catalysts containing crystalline gallium silicates with $SiO_2/Ga_2O_3$ molar ratios of 135, 165, or 195, acceptable performance can be obtained by subjecting them to the two-step treatment four, seven or ten times, respectively, whilst in order to attain optimum performance, the treatment should be carried out about 12, 21 or 30 times, respectively. As can be seen from the above, both for achieving acceptable performance and for achieving optimum performance the two-step treatment should be carried out more often according as the crystalline gallium silicate has a higher $SiO_2/Ga_2O_3$ molar ratio. In the process according to the invention both catalysts containing a crystalline gallium silicate with a high $SiO_2/Ga_2O_3$ molar ratio and catalysts in which the crystalline gallium silicate has a low $SiO_2/Ga_2O_3$ molar ratio may be used. The choice of $SiO_2/Ga_2O_3$ molar ratio is mainly determined by two factors, viz. the fairly high cost of gallium and the expense entailed in the two-step treatment. According as the crystalline gallium silicate present in the catalyst has a higher $SiO_2/Ga_2O_3$ molar ratio (viz. contains less gallium), the catalyst will be cheaper, but it will have to be subjected to the two-step treatment more often for its performance to be raised to an optimum level, which leads to an increase in cost. If, when using the present catalysts on a technical scale, it is the object to limit the number of two-step treatments to which the catalyst has to be subjected in order to bring its performance to an optimum level to less than 10, then this implies that in the process according to the invention preference is given to the use of catalysts containing a crystalline gallium silicate with a $SiO_2/Ga_2O_3$ molar ratio of at most 130.

It appears that the problem of catalysts containing a crystalline gallium silicate with a $SiO_2/Ga_2O_3$ molar ratio higher than 130 necessarily being preferred on account of their price, whereas on account of the expenses entailed in a large number of two-step treatments, required to carry the performance of these catalysts to an optimum level, they are certainly not to be preferred, can be solved in an attractive way. As already remarked hereinbefore, the investigation has revealed that the number of two-step treatments to be carried out in order to enhance the performance of a catalyst belonging to class I to attain a certain desired high level, can be considerably decreased if, before being subjected to the succession of two-step treatments, the catalysts are exposed to calcination at a temperature of 600°-1000° C. The minimum number of two-step treatments to be applied to catalysts containing a crystalline gallium silicate with a $SiO_2/Ga_2O_3$ molar ratio higher than 130, which catalysts have been subjected to previous calcination at 600°-1000° C., is given by the formula $$n = \frac{m - 100}{30}.$$

Subjecting the pre-calcined catalyst to a number of two-step treatments which corresponds to n (alternatively N+1) of the formula leads to the production of a catalyst with acceptable performance in the present conversion. Just as in the case of the catalysts which have not been subjected to previous calcination at 600°-1000° C., so in the case of the catalysts which have been subjected to such calcination it holds that performance, having been raised to an acceptable level by the use of the number of two-step treatments indicated by the formula, can be further enhanced to attain an optimum level by increasing the number of two-step treatments. The investigation has shown that the number of times that the catalysts which have undergone previous calcination at 600°-1000° C. are to be subjected to the two-step treatment in order to attain optimum performance is about twice the number (n, alternatively N+1) which, according to the formula, is the minimum required to achieve acceptable performance. For instance, for the aforementioned catalysts containing crystalline gallium silicates with $SiO_2/Ga_2O_3$ molar ratios of 135, 165 or 195 if subjected to previous calcination at 600°-1000° C., acceptable performance can be achieved by subjecting them to the two-step treatment twice, three or four times, respectively, whilst for attaining optimum performance these catalysts should be subjected to the treatment about four, six or eight times, respectively. If, when using the present catalysts on a technical scale—as with the catalysts which have not undergone previous calcination at 600°-1000° C.—it is the object to limit the number of times that the catalyst is to be subjected to the two-step treatment in order to bring its performance to an optimum level to less than 10, then, in the process according to the invention using catalysts which have undergone calcination at 600°-1000° C. preceding the succession of two-step treatments, the catalysts used by preference are those containing a crystalline gallium silicate with a $SiO_2/Ga_2O_3$ molar ratio of at most 220. When catalysts are used which have undergone calcination at 600°-1000° C. preceding the succession of two-step treatments, special preference is given to the use of catalysts containing a crystalline gallium silicate with the $SiO_2/Ga_2O_3$ molar ratio of 130-220.

In the first step of the two-step treatment the catalyst should be contacted for at least 15 minutes and at a temperature of 400°-650° C. with a reducing gas containing at least 20%v hydrogen. The first step is preferably carried out at a temperature of 475°-575° C. and using a reducing gas containing at least 40%v hydrogen. The first step can very suitably be carried out by using a gas which, in addition to hydrogen, contains either substantially nitrogen, or substantially carbon monoxide, or substantially $C_4^-$ hydrocarbons. Suitable gases which in addition to hydrogen contain substantially carbon monoxide may be obtained as synthesis gas, from a heavy carbonaceous material, such as coal, by gasification, or from light hydrocarbons, such as natural gas, by steam reforming or partial oxidation. Suitable gases which in addition to hydrogen contain substantially $C_4^-$ hydrocarbons may be obtained as a byproduct in the catalytic conversion of hydrocarbons in the presence of hydrogen, such as cracking, isomerization and reforming.

In the second step of the two-step treatment the catalyst should be contacted for at least 15 minutes and at a temperature of 350°-700° C. with an oxidizing gas containing at least 5%v oxygen. The first step is preferably carried out at a temperature of 475°-575° C. and by using an oxidizing gas containing at least 10%v oxygen. The first step can very suitably be carried out by using a gas which in addition to oxygen, contains either substantially nitrogen, or substantially nitrogen, carbon monoxide and carbon dioxide. A suitable gas which in addition to oxygen contains substantially nitrogen, is air. Suitable gases which in addition to oxygen contain substantially nitrogen, carbon monoxide and carbon dioxide are exhaust gases produced in the removal by excess air of coke from deactivated hydrocarbon conversion catalysts. The first and the second step of the two-step treatment are preferably carried out at the same temperature.

The preparation of the crystalline gallium silicates used in the process according to the invention can very suitably be carried out starting from an aqueous mixture comprising the following compounds: one or more compounds of an alkali metal (M), one or more organic nitrogen compounds (RN) which contain an organic cation or from which an organic cation is formed during the preparation of the silicate, one or more silicon compounds, one or more gallium compounds and, if desired, one or more compounds of a trivalent metal Y. The preparation is carried out by maintaining the mixture at an elevated temperature until the silicate has formed, and subsequently separating the silicate crystals from the mother liquor and washing, drying and calcining the crystals. In the aqueous mixture from which the silicates are prepared the various compounds should be present in the following molar ratios expressed—with the exception of the organic nitrogen compounds—in moles of the oxides:

$M_2O:SiO_2 = 0.01-0.35$,
$RN:SiO_2 = 0.02-1.0$,
$SiO_2:Ga_2O_3 = 25-400$,
$Y_2O_3:Ga_2O_3 < 1$, and
$H_2O:SiO_2 = 5-65$.

In the preparation of the silicates the base mixture may very suitably be a mixture containing a quaternary ammonium compound as organic nitrogen compound, a sodium compound as alkali metal compound and amorphous silica as silicon compound.

In the process according to the invention preference is given to the use of crystalline gallium silicates which have been prepared by crystallization from an aqueous mixture which, apart from possible impurities present in the reaction components, contains no compounds of a trivalent metal Y.

The silicates prepared as described hereinbefore contain alkali metal ions. By using suitable exchange methods these can be replaced by other cations, such as hydrogen ions or ammonium ions. The crystalline gallium silicates used in the process according to the invention preferably have an alkali metal content of less than 0.05%w. In the process according to the invention the crystalline gallium silicates may be used per se or in combination with a binder material, such a kaolin or bentonite.

The invention is now elucidated with the aid of the following example.

EXAMPLE

Two crystalline gallium silicates (silicates 1 and 2) were prepared by heating mixtures of NaOH, amorphous silica, $(C_3H_7)_4NOH$ and $Ga(NO_3)_3$ in water, in an autoclave under autogeneous pressure, at 150° C. for 24 hours. After cooling of the reaction mixtures the silicates formed were filtered off, washed with water until the pH of the wash water was about 8 and dried at 120° C. After one hour's calcination in air at 500° C. silicates 1 and 2 had the following properties (a) an X-ray powder diffraction pattern substantially corresponding with that mentioned in Table B, and (b) a $SiO_2/Ga_2O_3$ molar ratio of 70 for silicate 1 and 160 for silicate 2.

From silicates 1 and 2 were prepared silicates I and II, respectively, by boiling silicates 1 and 2 with a 1.0 molar $NH_4NO_3$ solution, washing with water, boiling again with a 1.0 molar $NH_4NO_3$ solution and washing, drying at 120° C. and calcination at 500° C.

Samples of silicates I and II were repeatedly subjected to a two-step treatment comprising a step in which the silicate was contacted for 30 minutes at a temperature of 550° C. and a pressure of 1.5 bar with an $H_2/N_2$ mixture in the volume ratio 1:1, followed by a second step in which the silicate was contacted for 1 hour at a temperature of 550° C. and a pressure of 1.5 bar with air. From silicates I and II were thus produced catalysts IA and IB and IIA–IIE, respectively. In addition two samples of silicate II were first contacted with air for 1 hour at 700° C. and then repeatedly subjected to the two-step treatment described hereinbefore. From silicate II were thus produced catalyst IIF and IIG.

Catalysts I–IB and II–IIIG were tested in eleven experiments (Experiments 1–11) in the preparation of $C_5+$ aromatic hydrocarbon mixtures starting from n-butane. The experiments were carried out in a reactor containing a fixed catalyst bed. Experiments 1–3 were carried out at a temperature of 575° C., a pressure of 1.5 bar and a space velocity of 4 $kg.kg^{-1}.hour^{-1}$ and Experiments 4–11 were carried out at a temperature of 550° C., a pressure of 1.5 bar and a space velocity of 2 $kg.kg^{-1}.h^{-1}$. The results of the experiments are listed in Table C. Table C also indicates how many times each silicate was subjected to the two-step treatment.

Of the experiments mentioned in Table C Experiments 2, 3 and 6–11 are experiments according to the invention. These experiments were carried out by using as catalysts crystalline gallium silicates which had been subjected to a number of two-step treatments according to the invention. These catalysts show high activity and high $H_2$ and $C_5+$ selectivities. Experiments 1, 4 and 5 fall outside the scope of the invention. They have been included in the patent application for comparison. Experiments 1 and 4 were carried out using as catalysts crystalline gallium silicates, but these gallium silicates had not been subjected to a two-step treatment according to the invention. In Experiment 5 (carried out using a crystalline gallium silicate with a $SiO_2/Ga_2O_3$ molar ratio of 160) the gallium silicate was subjected to the two-step treatment no more than three times, whereas the formula which expressed the relation between minimum number of times for the two-step treatment to be carried out and $SiO_2/Ga_2O_3$ molar ratio of the silicate stipulates that this number should be at least six.

On the results listed in Table C the following may be remarked. Comparison of the results of Experiments 1–3 shows that Catalyst I per se shows acceptable performance, which is enhanced by subjecting the catalyst three times (Experiment 2) or eight times (Experiment 3) to the two-step treatment. Comparison of the results of Experiments 4–9 shows that Catalyst II shows unacceptable performance, which is insufficiently improved by subjecting the catalyst three times (Experiment 5) to the two-step treatment. Subjecting Catalyst II to the two-step treatment eight times (Experiment 6) or 16 times (Experiment 7) leads to acceptable performance. Subjecting Catalyst II to the two-step treatment 20 times (Experiment 8) leads to optimum performance. This performance does not improve significantly when the number is raised from 20 to 30 (Experiment 9). Comparison of the results of Experiments 6 and 10 shows that the number of two-step treatments needed to achieve acceptable performance can be dramatically reduced (from 8 to 3) when the crystalline gallium silicate is subjected to calcination at 700° C. before being subjected to a succession of two-step treatments. Comparison of the results of Experiments 9 and 11 shows that there is no marked difference between the performance of the catalyst which has been subjected to a number of two-step treatments and the performance of the same catalyst which has been subjected to the two-step treatment the same number of times, but which, before being subjected to the two-step treatments, was subjected to calcination at 700° C.

TABLE C

| Experiment No. | 1 | 2 | 3 | 4 | 5 | 6 | 7 | 8 | 9 | 10 | 11 |
|---|---|---|---|---|---|---|---|---|---|---|---|
| Catalyst No. | I | IA | IB | II | IIA | IIB | IIC | IID | IIE | IIF | IIG |
| number of times that silicate was subjected to two-step treatment | — | 3 | 8 | — | 3 | 8 | 16 | 20 | 30 | 3* | 30* |
| Conversion, % w | 91 | 95 | 97 | 60 | 66 | 76 | 90 | 92 | 91 | 78 | 89 |
| Product selectivity, % w on converted material | | | | | | | | | | | |
| $H_2$ | 4.0 | 4.4 | 5.0 | 2.0 | 2.9 | 3.9 | 4.0 | 5.3 | 5.4 | 3.9 | 5.3 |
| $C_1-C_3$ | 47.0 | 36.2 | 32.2 | 65.0 | 60.2 | 48.6 | 41.1 | 38.3 | 36.8 | 49.7 | 38.1 |
| iso—$C.°_4$ | 2.0 | 1.0 | 1.2 | 7.2 | 6.6 | 6.3 | 3.7 | 3.4 | 4.9 | 4.4 | 2.0 |
| $\Sigma C_4=$ | 1.4 | 0.5 | 0.3 | 5.0 | 3.8 | 3.0 | 2.5 | 2.8 | 1.9 | 3.5 | 1.9 |
| $C_5+$ | 45.6 | 57.9 | 61.3 | 20.8 | 26.5 | 38.2 | 48.7 | 50.2 | 51.0 | 38.5 | 52.7 |

*After previous treatment with air at 700° C.

What is claimed is:

1. A process for the preparation of an aromatic hydrocarbon mixture, characterized in that one or more paraffins with two, three or four carbon atoms per molecule or aliphatic hydrocarbon mixtures consisting more than 50%w of said paraffins are contacted with a catalyst comprising a crystalline gallium silicate which (a) has been prepared by crystallization from an aqueous mixture which, in addition to the components needed for the synthesis of the silicate, comprises one or more gallium compounds in such quantities that in the composition of the silicate expressed in moles of the oxides, the $SiO_2/Ga_2O_3$ molar ratio is 25–250 and (b) after one hour's calcination in air at 500° C. has an X-ray powder diffraction pattern in which the strongest lines are the four lines mentioned in Table A,

TABLE A d(Å)

11.1 ± 0.2

10.0 ± 0.2

3.84 ± 0.007

3.72 ± 0.06, wherein the catalyst is subjected at least once before contact with said aliphatic hydrocarbon to a two-step treatment involving a step in which the catalyst is contacted for at least 15 minutes and at a temperature of 400°–650° C. with a reducing gas containing at least 20%v hydrogen, followed thereafter by a second step in which the catalyst is contacted for at least 15 minutes and at a temperature of 350°–700° C. with an oxiding gas containing at least 5%v oxygen, wherein the minimum number of two-step treatments for a catalyst with a $SiO_2/Ga_2O_3$ molar ratio higher than 110 is represented by the formula $$n = \frac{m - 100}{10}$$

wherein n represents the minimum number of two-step treatments and m represents the $SiO_2/Ga_2O_3$ molar ratio of the silicate, and if the value for n is expressed as the sum of a natural number N and a fractional number smaller than 1 is determined then, the number of two-step treatments that the catalyst is subjected to is N+1.

2. The process as claimed in claim 1, characterized in that said aqueous mixture contains one or more compounds of a trivalent metal Y selected from the group consisting of aluminum, iron, cobalt and chromium and that the $Y_2O_3/Ga_2O_3$ molar ratio is lower than 1.

3. The process as claimed in claim 1, characterized in that before said catalyst is subjected to said two-step treatment or a succession of two-step treatments, the catalyst is calcined at a temperature of 600°–1000° C. and that for catalysts having a $SiO_2/Ga_2O_3$ molar ratio higher than 130, then the minimum number of two-step treatment is represented by the formula $$n = \frac{m - 100}{30}.$$

4. The process as claimed in claim 2, characterized in that before said catalyst is subjected to said two-step treatment or succession of two-step treatments, the catalyst is calcined at a temperature of 600°–1000° C. and that for catalysts having a $SiO_2/Ga_2O_3$ molar ratio higher than 130, then the minimum number of two-step treatments is represented by the formula $$n = \frac{m - 100}{30}.$$

5. The process as claimed in claim 1, characterized in that said feedstock contains more than 75%w of one or more paraffins having three or four carbon atoms per molecule.

6. The process as claimed in claim 5, characterized in that the feedstock consists substantially completely of one or more paraffins having three or four carbon atoms per molecule.

7. The process as claimed in claim 6, characterized in that the feed consists of a mixture of paraffins with three and four carbon atoms per molecule, which has been obtained as a by-product in the production of mineral oil.

8. The process as claimed in claim 1, characterized in that the aromatic hydrocarbon is prepared at a temperature of 350°–700° C., a pressure of 1–20 bar and a space velocity of $0.1-10 \text{ kg.kg}^{-1}.\text{h}^{-1}$.

9. The process as claimed in claim 8, characterized in that the aromatic hydrocarbon is prepared at a temperature of 450°–650° C., a pressure of 1–10 bar and a space velocity of $0.5-5 \text{ kg.kg}^{-1}.\text{h}^{-1}$.

10. The process as claimed in claim 1, characterized in that the crystalline gallium silicate has a $SiO_2/Ga_2O_3$ molar ratio of at least 60.

11. The process as claimed in claim 1, characterized in that the catalyst comprises a crystalline gallium silicate having a $SiO_2/Ga_2O_3$ molar ratio of not more than 110 and that said silicate is subjected to said two-step treatment not more than three times.

12. The process as claimed in claim 1, characterized in that the catalyst comprises a crystalline gallium silicate having a $SiO_2/Ga_2O_3$ molar ratio between 110 and 130, and that the number of times that said silicate is subjected to said two-step treatment is about three times the number derived by said formula as the minimum number of treatment times.

13. The process as claimed in claim 3, characterized in that the catalyst comprises a crystalline gallium silicate having a $SiO_2/Ga_2O_3$ molar ratio between 130 and 220, and that the number of times that said silicate is subjected to said two-step treatment following calcination at 600°–1000° C. is about twice the number derived by said formula as the minimum number of treatment times.

14. The process as claimed in claim 1, characterized in that said reducing gas contains at least 40%v hydrogen.

15. The process as claimed in claim 1, characterized in that said oxidizing gas contains at least 10%v oxygen.

16. The process as claimed in claim 1, characterized in that the two steps of said two-step treatment are carried out at a temperature of 475°–575° C.

17. The process as claimed in claim 16, characterized in that the two steps of said two-step treatment are carried out at the same temperature.

18. The process as claimed in claim 2, characterized in that the crystalline gallium silicate is prepared by maintaining an aqueous mixture comprising the following compounds: one or more compounds of an alkali metal (M), one or more organic nitrogen compounds (RN) which contain an organic cation or from which an organic cation is formed during the preparation of the silicate, one or more silicon compounds, one or more gallium compounds and, if desired, one or more compounds of a trivalent metal Y, in which mixture the various compounds are present in the following molar ratios, expressed—with the exception of the organic nitrogen compounds—in moles of the oxides:

$M_2O:SiO_2 = 0.01-0.35$,
$RN:SiO_2 = 0.02-1.0$,
$SiO_2:Ga_2O_3 = 25-400$,
$Y_2O_3:Ga_2O_3 = <1$, and $H_2O:SiO_2 = 5-65$ at an elevated temperature until silicate crystals are formed which are separated from the mother liquor and then calcined in air.

19. The process as claimed in claim 18, characterized in that said organic nitrogen compound is a quaternary ammonium compound, said alkali metal compound is a sodium compound and said silicon compound is amorphous silica.

20. The process as claimed in claim 19, characterized in that said crystalline silicate is prepared by crystallization from said aqueous mixture which, apart from impurities present in the reaction components, contains no compounds of a trivalent metal Y.

* * * * *